(12) United States Patent
Stapleton et al.

(10) Patent No.: US 8,338,476 B2
(45) Date of Patent: Dec. 25, 2012

(54) **COMPOSITIONS AND METHODS OF SENSITIZING METHICILLIN RESISTANT *STAPHYLOCOCCUS AUREUS* TO BETA-LACTAM ANTIBIOTICS**

(75) Inventors: Paul Stapleton, London (GB); Yukihiko Hara, Tokyo (JP); Peter Taylor, West Sussex (GB)

(73) Assignees: Mitsui Norin Co, Ltd., Tokyo (JP); The School of Pharmacy, University of London, London (GB)

( * ) Notice: Subject to any disclaimer, the term of this patent is extended or adjusted under 35 U.S.C. 154(b) by 785 days.

(21) Appl. No.: 12/095,960

(22) PCT Filed: Dec. 29, 2005

(86) PCT No.: PCT/US2005/047570
§ 371 (c)(1),
(2), (4) Date: Sep. 1, 2009

(87) PCT Pub. No.: WO2007/075176
PCT Pub. Date: Jul. 5, 2007

(65) Prior Publication Data
US 2010/0035979 A1    Feb. 11, 2010

(51) Int. Cl.
*A61K 31/352* (2006.01)
*A61K 31/397* (2006.01)
*A01N 43/16* (2006.01)
*A01N 43/44* (2006.01)
*A01N 43/90* (2006.01)

(52) U.S. Cl. .................... 514/456; 514/210.02

(58) Field of Classification Search .............. 514/456, 514/210.02
See application file for complete search history.

(56) References Cited

U.S. PATENT DOCUMENTS

| 5,358,713 | A | 10/1994 | Shimamura |
| 5,807,564 | A | 9/1998 | Shimamura et al. |
| 5,879,683 | A | 3/1999 | Hamilton-Miller |
| 6,652,890 | B2 | 11/2003 | Morre et al. |
| 6,939,860 | B2 * | 9/2005 | Netke et al. ............. 514/27 |

FOREIGN PATENT DOCUMENTS

| EP | 0443090 | 8/1991 |
| EP | 761226 | 3/1997 |
| EP | 1504754 | 9/2005 |
| JP | 9-132532 | 5/1997 |
| WO | 2005034976 | 4/2005 |

OTHER PUBLICATIONS

Nakagawa et al. J. Agric. Food Chem., 1999, 47, p. 3967-3973.*
FDA Guidance for Industry on Container Closure Systems for Packaging Human Drugs and Biologics, May 1999.*
Shiota et al; Marked Reduction in the Minimum Inhibitory Concentration (MIC) of B-Lactams in Methicillin-Resistant *Staphyloccus aureus* Produced by Epicatechin Gallate, an Ingredient of Green Tea (*Camellia sinensis*); Biol. Pharm Bull. 22(12)1388-1390 (1999), vol. 22, No. 12.
Taylor, et al; New Ways to Treat Bacterial Infections, Reviews; Therapeutic Focus; DDT vol. 7, No. 21; Nov. 2002.
Stapleton, et al; Modulation of B-lactam resistance in *Staphylococcus aureus* by catechins and gallates; International Journal of Antimicrobial Agents; vol. 23, No. 5; May 2004.
Hamilton-Miller, et al; Activity of the tea component epicatechin gallate and analogues against methicillin-resistant *Staphylococcus aureus*; The Journal of Antimicrobial Chemotherapy; vol. 46, No. 5; Nov. 2000.
Zhao, et al; Mechanism of synergy between epigallocatechin gallate and beta-lactams against methicillin-resistant *Staphylococcus aureus*; Antimicrobial Agents and Chemotherapy; vol. 45, No. 6; Jun. 2001.
Yamada, et al; Effects of tea catechin inhalation on methicillin-resistant *Staphylococcus aureus* in elderly patients in a hospital ward; Journal of Hospital Infection; vol. 53, No. 3; Mar. 2003.
Taguri, T., "MRSA", Pharmacia, Feb. 2007, vol. 43, No. 2, pp. 162-163.
Shiota, S., et al., "Marked Reudction in the Minimum Inhibitory Concentration (MIC) of B-Lactams in Methicillin-Resistant *Staphylococcus aureus* Produced by Epicatechin Gallate, an Ingredient of Green Tea (*Camellia sinensis*)", Biological Pharmacology Bulletin, 1999, vol. 22, No. 12, pp. 1388-1390.

* cited by examiner

*Primary Examiner* — Shaojia Anna Jiang
*Assistant Examiner* — Jonathan S Lau
(74) *Attorney, Agent, or Firm* — Fish & Associates, PC

(57) ABSTRACT

Contemplated methods and compositions further increase susceptibility of sensitized MRSA against various antibiotic drugs. Most preferably, the MRSA is already sensitized with a galloylated catechin (e.g., ECG), and further sensitization is achieved by exposure to a non-galloylated catechin (e.g., EC), and most preferably the corresponding non-galloylated catechin.

11 Claims, 3 Drawing Sheets

| Compound (µg/ml) | | S. aureus BB568 Oxacillin MIC (µg/ml) determined in the presence of ECg (µg/ml) | | | | S. aureus EMRSA-16 Oxacillin MIC (µg/ml) determined in the presence of ECg (µg/ml) | | | | S. aureus EMRSA-15 Oxacillin MIC (µg/ml) determined in the presence of ECg (µg/ml) | | | |
|---|---|---|---|---|---|---|---|---|---|---|---|---|---|
| | | 0 | 3.12 | 6.25 | 12.5 | 0 | 3.12 | 6.25 | 12.5 | 0 | 3.12 | 6.25 | 12.5 |
| | 0 | 256 | 64 | 8 | 1 | 512 | 128 | 8 | 1 | 16 | 1 | 0.5 | 0.25 |
| EC | 6.25 | 256[c] | 8 | 1 | 0.5 | 512 | 8 | 1 | 0.5 | 16 | 0.5 | 0.25 | 0.25 |
| | 12.5 | 256 | 4 | 0.5 | 0.5 | 512 | 8 | 0.5 | 0.5 | 16 | 0.5 | 0.25 | 0.25 |
| | 25 | 256 | 2 | 0.5 | 0.5 | 512 | 1 | 0.5 | NG[b] | 16 | 0.5 | 0.25 | 0.12 |
| | 50 | nd[a] | nd[a] | nd[a] | nd[a] | 512 | 0.5 | NG[b] | NG[b] | nd[a] | nd[a] | nd[a] | nd[a] |
| EGC | 6.25 | 256 | 32 | 1 | 0.5 | 512 | 32 | 1 | 0.5 | 16 | 0.5 | 0.25 | 0.25 |
| | 12.5 | 256 | 8 | 1 | 0.5 | 512 | 16 | 1 | 0.5 | 16 | 0.5 | 0.25 | 0.12 |
| | 25 | 128 | 4 | 0.5 | 0.5 | 512 | 8 | 0.5 | NG[b] | 8 | 0.25 | 0.12 | 0.12 |
| | 50 | nd[a] | nd[a] | nd[a] | nd[a] | 512 | 2 | NG[b] | NG[b] | nd[a] | nd[a] | nd[a] | nd[a] |
| EGCg | 6.25 | 128 | 32 | 16 | 8 | 256 | 128 | 32 | 16 | 4 | 1 | 1 | 0.5 |
| | 12.5 | 64 | 32 | 32 | 8 | 128 | 128 | 32 | 32 | 1 | 1 | 1 | 1 |
| | 25 | 32 | 16 | 16 | 8 | 64 | 32 | 8 | 4 | 1 | 1 | 1 | 0.5 |

Figure 2A

| Compound (µg/ml) | S. aureus BB568 Oxacillin MIC (µg/ml) determined in the presence of EGCg (µg/ml) | | | | S. aureus EMRSA-16 Oxacillin MIC (µg/ml) determined in the presence of EGCg (µg/ml) | | | | S. aureus EMRSA-15 Oxacillin MIC (µg/ml) determined in the presence of EGCg (µg/ml) | | | |
|---|---|---|---|---|---|---|---|---|---|---|---|---|
| | 0 | 6.25 | 12.5 | 25 | 0 | 6.25 | 12.5 | 25 | 0 | 6.25 | 12.5 | 25 |
| 0 | 256 | 128 | 64 | 32 | 512 | 256 | 128 | 64 | 8 | 4 | 1 | 1 |
| EC 6.25 | 256 | 64 | 64 | 16 | 512[a] | 256 | 256 | 128 | 16 | 4 | 2 | 0.5 |
| 12.5 | 256 | 64 | 32 | 16 | 512 | 256 | 256 | 128 | 16 | 4 | 2 | 0.5 |
| 25 | 256 | 64 | 32 | 8 | 512 | 256 | 256 | 128 | 16 | 2 | 1 | 0.5 |
| EGC 6.25 | 256 | 64 | 32 | 16 | 512 | 256 | 128 | 64 | 16 | 2 | 1 | 0.50 |
| 12.5 | 256 | 64 | 32 | 8 | 512 | 128 | 64 | 16 | 16 | 2 | 0.5 | 0.25 |
| 25 | 128 | 32 | 16 | 1 | 512 | 64 | 8 | 2 | 8 | 2 | 0.5 | 0.125 |

Figure 2B

COMPOSITIONS AND METHODS OF SENSITIZING METHICILLIN RESISTANT *STAPHYLOCOCCUS AUREUS* TO BETA-LACTAM ANTIBIOTICS

FIELD OF THE INVENTION

The field of the invention is antibiotic treatment compositions and methods, and particularly treatment of methicillin resistant *Staphylococcus aureus* (MRSA) that include synergistic combinations of selected catechins.

BACKGROUND OF THE INVENTION

Epigallocatechin gallate (EGCG) and other tea catechins have previously been used as antibacterial agents, and examples for such activity are well known in the art (see e.g., *Jpn. J. Bacteriol.* (1991); 46: 839-845). However, to exhibit significant antibacterial effect, dosages are generally very high and are therefore typically not achieved in physiological conditions or in vivo. Similar high concentrations were reported by Shimamura in U.S. Pat. No. 5,358,713 using selected catechins to prevent transmission of MRSA to another person.

To reduce minimum inhibitory concentration of certain antibiotic drugs, antibiotic drugs were combined with certain catechins, and selected catechins were reported to be sensitizing agents for amikacin, chloramphenicol, and various beta-lactam antibiotics as described by Shimamura in U.S. Pat. No. 5,807,564. Similarly, rose polyphenols were reported to reduce the minimum inhibitory concentration of various beta-lactam antibiotics (see e.g., *Microbiol Immunol.* 2004; 48(1):67-73.). However, and at least for some of the catechins, the effective concentrations require were still relatively high. In other attempts to treat MRSA infections, selected catechins were also combined with specific theaflavin compounds as described in EP 0 761 226 to produce an antimicrobial composition. Unfortunately, the same difficulties remained with respect to certain catechins. In yet further known combinations of selected catechins, Morree et al disclosed in U.S. Pat. No. 6,652,890 a mixture of EGC and EC that was effective in inhibiting NADH oxidase of neoplastic cells that express NOX to thereby treat cancer. However, the effect of such combination on bacteria was not reported in that reference.

In still further known attempts to use catechins as antibiotic drugs, various catechins were chemically modified as described by Stapleton et al in WO 2005/034976. While such modified catechins provided remarkable antibacterial effect as compared to their unmodified counterparts, synthesis and purification increases cost, and administration to human has not yet been proven safe and effective.

Thus, while numerous compositions and methods for eradicating and/or sensitizing MRSA to various antibiotics are known in the art, all or almost all of them suffer from one or more disadvantages. Therefore, there is still a need for improved pharmaceutical agents for treatment and/or chemoprevention of infections with MRSA.

SUMMARY OF THE INVENTION

The present invention is directed to the discovery that some non-galloylated catechins will increase sensitization of MRSA against selected antibiotics, where the selected antibiotic is already combined with a galloylated catechin.

In one aspect of the inventive subject matter, a method of reducing MIC (minimum inhibitory concentration) of an antibiotic drug in a methicillin resistant strain of *S. aureus* includes a step of exposing the *S. aureus* to a galloylated catechin at a concentration effective to reduce the MIC of the antibiotic drug to a first level. In a further step, it is recognized that application of a non-galloylated catechin synergistically further decreases the MIC of the antibiotic drug from the first level to a second level, and in still another step, the *S. aureus* is exposed to the non-galloylated catechin in the presence of the galloylated catechin at a concentration effective to reduce the MIC of the antibiotic drug to the second level.

Most preferably, the antibiotic drug may be characterized as a beta-lactam antibiotic (e.g., oxacillin, methicillin, penicillin), as a tetracycline-type antibiotic, (e.g., tetracycline, quatrimycin, epitetracycline, etc.), and/or as a chloramphenicol-type antibiotic drug (e.g., chloramphenicol, dextramycin, 1-deoxychloramphenicol, etc.), the galloylated catechin is ECG or EGCG, and/or the non-galloylated catechin is EC or EGC. Depending on the particular combination, it is contemplated that the first level is equal or less than 50% of the MIC of the antibiotic drug without exposing the *Staphylococcus aureus* to the galloylated catechin, and/or the second level is equal or less than 5% of the MIC of the antibiotic drug without exposing the *Staphylococcus aureus* to the galloylated catechin.

In other contemplated aspects, the first level is equal or less than 5% of the MIC of the antibiotic drug without exposing the *Staphylococcus aureus* to the galloylated catechin, and the second level is equal or less than 0.5% of the MIC of the antibiotic drug without exposing the *Staphylococcus aureus* to the galloylated catechin. Therefore, in at least some examples, the *Staphylococcus aureus* is exposed to the galloylated catechin at a concentration of less than 10 microgram/ml, and to the non-galloylated catechin at a concentration of equal or less than 50 microgram/ml.

Viewed from a different perspective, the inventors also contemplate a method of suppressing growth of a methicillin resistant strain of *Staphylococcus aureus* (e.g., BB568, EMRSA-16, or EMRSA-15) wherein in one step *Staphylococcus aureus* is exposed to a combination of a galloylated catechin and an antibiotic drug, wherein the galloylated catechin and the antibiotic drug are present at a concentration ineffective to suppress growth. In another step, the *Staphylococcus aureus* is exposed to a non-galloylated catechin in the presence of the combination at a concentration effective to suppress growth of the *Staphylococcus aureus*.

Similar to the method above, it is preferred that in such methods the antibiotic drug is a beta-lactam antibiotic at a concentration of 60 microgram/ml, and wherein the galloylated catechin is ECG at a concentration of 5 microgram/ml, and/or that the non-galloylated catechin (e.g., EC or EGC) is present at a concentration of at least 25 microgram/ml, and more typically at least 50 microgram/ml.

Therefore, in another aspect of the inventive subject matter, an antibiotic drug (e.g., beta-lactam antibiotic) composition includes a galloylated catechin and a non-galloylated catechin, wherein the non-galloylated catechin is present at a concentration to synergistically reduce a MIC of the antibiotic drug with respect to the galloylated catechin. Contemplated compositions further include an information associated with the composition that the galloylated catechin and the non-galloylated catechin are present in a synergistic combination effective to reduce the MIC of the antibiotic drug with respect to the galloylated catechin.

Most preferably, the galloylated catechin is ECG or EGCG, while the non-galloylated catechin is EC or EGC. Typically, the non-galloylated catechin and the galloylated catechin are present in a weight ratio of at least 3:1, and even more typically in a weight ratio of at least 6:1. While it should be appreciated that the composition may be formulated in numerous manners, topical formulations (e.g., spray, cream, ointment, etc.) are particularly preferred.

Various objects, features, aspects and advantages of the present invention will become more apparent from the following detailed description of preferred embodiments of the invention.

BRIEF DESCRIPTION OF THE DRAWINGS

FIG. 2A is a table summarizing the effects of EC, EGC, and EGCG on the capacity of ECG to sensitize selected S. aureus strains to oxacillin.

FIG. 2B is a table summarizing the effects of EC and EGC on the capacity of EGCG to sensitize S. aureus strains to oxacillin.

DETAILED DESCRIPTION

Figure 1:
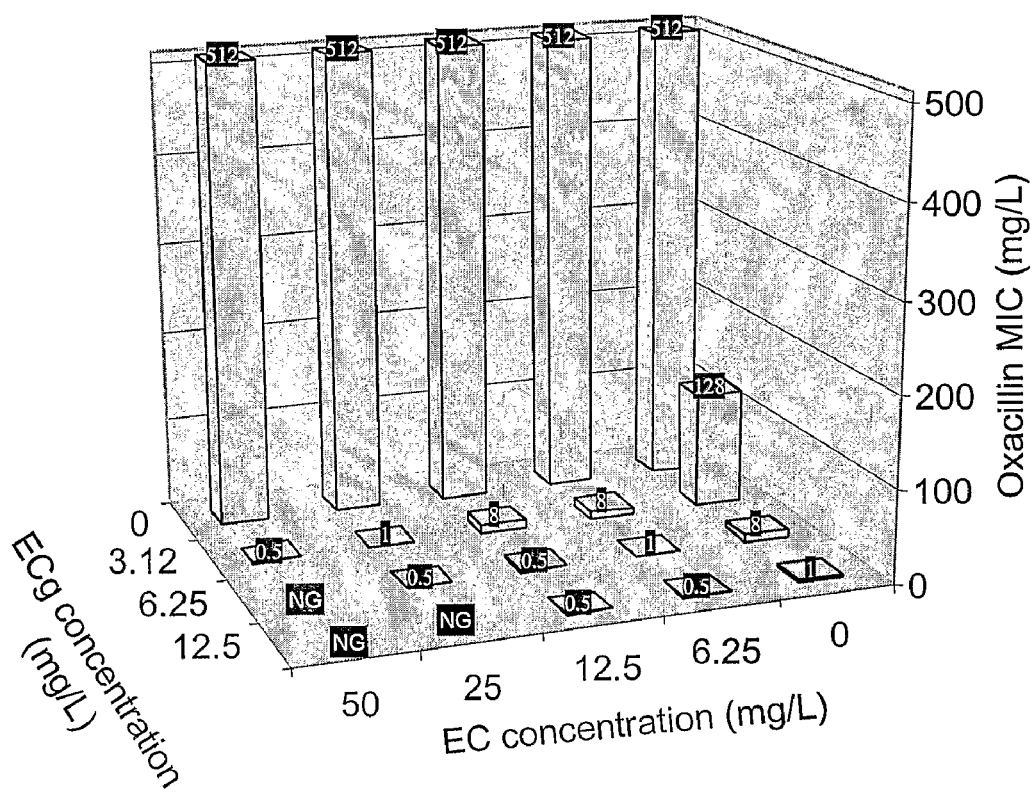
FIG. 1 is a graph depicting synergistic effects of the combination of EC and ECG on the MIC of oxacillin for EMRSA-16.

The inventors have unexpectedly discovered that catechin-mediated sensitization of MRSA against various antibiotic drugs using galloylated catechins can further be enhanced by combining the galloylated catechin with a non-galloylated catechin, and most preferably with the corresponding non-galloylated catechin. Remarkably, the non-galloylated catechins that promote sensitization to an antibiotic drug appear to have little or no effect on the minimum inhibitory concentration of the drug when used by themselves.

As used herein, the terms "MRSA", "methicillin resistant strain of Staphylococcus aureus", and "methicillin resistant Staphylococcus aureus" are used interchangeably herein and refer to S. aureus that is resistant to numerous, and more typically to all beta-lactam antibiotic drugs. Additional resistance may also be present with respect to cephalosporins and/or carbapenems. Hospital-associated MRSA isolates often are multiply resistant to other commonly used antimicrobial agents, including erythromycin, clindamycin, and tetracycline, while community-associated MRSA isolates are often resistant only to beta-lactam antibiotic drugs and erythromycin. Resistance is confirmed following protocols of the NCLS (National Committee for Clinical Laboratory Standards), and is typically reflected by an MIC of equal or greater than 4 microgram/ml in the Oxacillin MIC Test, a diffusion disk of equal or less than 10 mm or 19 mm in the Oxacillin Disk Diffusion Tests or Cefoxitin Disk Diffusion Test, respectively. As also used herein, the terms "minimum inhibitory concentration" and "MIC" are used interchangeably and refer to the minimum concentration of an antibacterial drug in a given culture medium below which bacterial growth is not inhibited.

The term "galloylated catechin" as also used herein refers to a compound in which the C-ring of the compound (for nomenclature, see Formula 1 below) is modified with a substituted or unsubstituted benzoic acid radical, and most typically a gallic acid ester radical. Most typically, the substituted or unsubstituted benzoic acid ester radical is covalently bound to the C-ring in the 3-position. Contemplated substituents on such substituted benzoic acids include one or more hydroxyl groups and their respective ester radicals, various alkylether radicals, amino groups, nitro groups, sulfate and/or phosphate groups, each of which may be further substituted.

In contrast, the term "non-galloylated catechin" as used herein refers to a compound in which the C-ring may or may not be modified with a substituent, but wherein that substituent, when present in the 3-position of the C-ring, is not a gallic acid ester radical. Thus, and among numerous other suitable substituents, the 3-position of the C-ring on non-galloylated catechins will be a hydrogen or hydroxy group.

In one preferred aspect of the inventive subject matter, the inventors incubated strain EMRSA-16 of Staphylococcus aureus with varying concentrations of the galloylated catechin epicatechin gallate (ECG) between 0 mcg/ml and 12.5 mcg/ml to increase sensitivity of the strain against oxacillin. MICs were then recorded and the experiments were repeated in the presence of the non-galloylated catechin epicatechin at varying concentrations between 0 mcg/ml and 50 mcg/ml. Remarkably, the addition of the non-galloylated catechin reduced the MIC in a significant and synergistic manner. Similar results were obtained when epicatechin was replaced with the non-galloylated epigallocatechin. In contrast, when the galloylated epigallocatechin gallate was employed, substantially no significant and synergistic effect was obtained.

While not wishing to be bound by any particular theory or hypothesis, the inventors contemplate that nanomolar concentrations of catechins may be able to modulate the structure and function of biological membranes through their capacity to partition into the phospholipid palisade. Galloylated catechins are thought to penetrate deeper into phosphatidylcholine and phosphatidylethanolamine bilayers than their non-galloylated analogues. Thus, it is expected that ECg and EGCg occupy a deeper location in the membrane, and that EC and EGC localize at a more shallow location (closer to the phospholipid—water interface). These differences in membrane penetration parallel the capacity of these molecules to modify staphylococcal beta-lactam resistance. Interestingly, the quantities of ECg and EGCg that are incorporated into lipid bilayers are markedly increased in the presence of EC, raising the possibility that the capacity of catechin gallates to reduce the level of staphylococcal beta-lactam resistance could be potentiated by non-galloylated catechins.

In other contemplated aspects of the inventive subject matter it should be appreciated that numerous galloylated catechins other than epicatechin gallate (ECG) are also deemed suitable for use herein. Among other galloylated catechins, it is contemplated that appropriate compounds include catechin gallate (CG), gallocatechin gallate (GCG), epigallocatechin gallate (EGCG), theaflavin monogallate A, theaflavin monogallate B, and theaflavin digallate. It should further be noted that the catechins (galloylated and non-galloylated) contemplated herein include optical isomers, chiral centers, and/or stereoisomers, and that all of such forms (and mixtures thereof) are contemplated herein. Similarly, non-galloylated catechins may include numerous alternative compounds, including catechin (C), gallocatechin (GC), and epigallocatechin (EGC).

Therefore, preferred galloylated and non-galloylated catechins contemplated herein will have a structure according to Formula 1

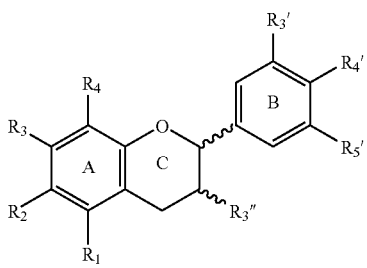

Formula 1 in which $R_1$, $R_2$, $R_3$, $R_4$, $R_3'$, $R_4'$, and $R_5'$ are independently H, OH, or M; wherein M is OC(O)R, OC(S)R, OC(NH)R, OR, or R, wherein R is optionally substituted alkyl, alkenyl, alkynyl, alkaryl, or aryl (and most preferably a mono-, di-, or trihydroxylated benzoic acid radical); wherein A, B, and C in the structure denote the respective rings; and where the catechin is a galloylated catechin, $R_3''$ is a gallic acid ester radical; and where the catechin is a non-galloylated catechin, $R_3''$ is M with the proviso that R is not a gallic acid radical in OC(O)R.

With respect to suitable concentrations of the galloylated catechin, it is generally contemplated that all concentrations are deemed appropriate so long as such concentration achieves at least some level of sensitization (i.e., reduces the MIC of an antibiotic drug as compared to growth under same conditions without galloylated catechin). Moreover, it should be recognized that different galloylated catechins will exhibit distinct reductions in MIC under comparable conditions. Still further, a suitable concentration of galloylated catechins may also at least in part be determined by a predetermined concentration of non-galloylated catechins. Therefore, various concentrations of galloylated catechins (including ECG) are contemplated and will generally be between 0 mcg/ml and 50 mg/ml (and even higher), but more typically between 1 mcg/ml and 1 mg/ml, and most typically between 5 mcg/ml and 100 mcg/ml.

Similarly, the concentration of contemplated non-galloylated catechins will vary and depend on numerous factors, including the particular chemical structure of the non-galloylated catechin, the concentration and type of the galloylated catechin, the bacterial strain, and/or the antibiotic drug. However, it is generally contemplated that the concentration of the non-galloylated catechin is between 0 mcg/ml and 50 mg/ml (and even higher), more typically between 1 mcg/ml and 1 mg/ml, and most typically between 5 mcg/ml and 100 mcg/ml. Furthermore, it is preferred (but not necessarily so) that the non-galloylated catechin is present in at least equimolar amounts, more preferably in molar excess of 1.1-2.0 to 1, even more preferably in molar excess of 2.0-4.0 to 1, and most preferably in molar excess of 2.0-10.0 to 1 with respect to the galloylated catechin.

Still further, it is preferred that the non-galloylated catechin is the corresponding catechin of the galloylated catechin. For example, where sensitization to a first level is effected by ECG, it is preferred that the non-galloylated catechin is EC. In another example, where sensitization to a first level is effected by EGCG, it is preferred that the non-galloylated catechin is EGC. However, it should also be appreciated that more than one catechin (galloylated and/or non-galloylated) may be employed in contemplated combinations. For example, sensitization to a first level may be effected by a mixture of catechins that includes at least one galloylated catechin, and the sensitization to a second, lower level may then be effected by a single non-galloylated catechin. On the other hand, and where desirable, sensitization to a first level may be effected by a single catechin, and the sensitization to a second, lower level may then be effected by a mixture that includes at least one non-galloylated catechin.

Where catechin mixtures are employed, it is particularly preferred that the mixture is isolated from a plant (e.g., tea plant, grape, blueberry, etc.). Such catechin isolates may be normalized to a specific formulation in which the ratio of galloylated to non-galloylated catechins is predetermined. For example, a typical percentage of individual catechins in a green tea extract with a dominating galloylated catechin proportion may be 10-15% EGCg, 2-3% ECG, 2% EC, and 2-3% EGC (e.g., Suganuma et al., 1999, Can. Res. 59:44-47). On the other hand, extracts may be prepared or modified to have predominantly non-galloylated catechins (e.g., with 10-20% of EGC and EC, 2-3% ECG, and 5% EGCG). In addition, caffeine, theobromine, theophylline, and phenolic acids, such as gallic acid, may also be present as constituents of green tea extracts, and are typically present in smaller quantities than the polyphenols. Among other contemplated extracts, particularly suitable polyphenol extracts include polyphenon E and polyphenon B, both of which are commercially available from Mitsui Norin Japan (1-2-9 Nishishinbashi, Minato-ku, Tokyo, 105-8427, Japan), and which may be employed as further base material for specific preparations.

With respect to the antibiotic drugs, it is generally contemplated that non-galloylated catechins may further increase sensitivity (i.e., reduce MIC) of previously sensitized MRSA to numerous antibiotic drugs, including all or almost all beta-lactam antibiotics, tetracyclines, and/or chloramphenicol-type drugs. Thus, and among other antibiotic drugs, contemplated antibiotics include various penicillins (e.g., benzathine penicillin, benzylpenicillin (penicillin G), phenoxymethylpenicillin (penicillin V), dicloxacillin, flucloxacillin, amoxicillin, ampicillin, etc.), various cephalosporins (e.g., cephalexin, cephalothin, cephazolin, cefuroxime, cefamandole, ceftriaxone, cefotaxime, etc.), various carbapenems (e.g., imipenem, meropenem, ertapenem, etc.), monobactams (e.g., aztreonam), various tetracyclins (e.g., tetracycline, quatrimycin, epitetracycline, etc.), and various chloramphenicol-type antibiotic drugs (e.g., chloramphenicol, dextramycin, 1-deoxychloramphenicol, etc.).

Depending on the type of antibiotic drug and concentration of galloylated catechin, it should be appreciated that the increase in sensitivity using the non-galloylated catechin may vary considerably. However, it is generally contemplated that the increase in sensitivity (i.e., reduction in MIC) is at least 2-fold (e.g., from 20 mcg/ml to 10 mcg/ml), more typically at least 3-fold, even more typically 4-6 fold, and most typically at least 5-10 fold (e.g., from 50 mcg/ml to 10 mcg/ml).

It is still further contemplated that exposure of the MRSA to the galloylated and/or non-galloylated catechin is preferably, but not necessarily performed in the presence of the antibiotic drug. Most typically (but again not necessarily), the galloylated and non-galloylated catechin are administered together to the environment in which the MRSA is present. For example, and especially where the administration is ex vivo or a topical administration (e.g., disinfectant spray, in vitro culture, topical ointment, etc.), the catechin combination may be admixed to the antibiotic solution. In another example, and especially where the combination is administered to a mammal, the catechin combination may also be administered orally and separately from the antibiotic preparation (which may or may not be administered orally or parenterally).

Therefore, it should be recognized that the galloylated and/or non-galloylated catechin may be administered in numerous formulations, and especially preferred formulations include oral formulations in solid (e.g., isolated catechin, or polyphenol powder from tea extracts) or liquid form (e.g., liquid catechin preparation or tea extract). Further particularly preferred formulations include topical formulations (e.g., as cream, ointment, gel, lotion, etc.). There are numerous such commercially available formulations known in the art, and all of those are deemed suitable for use herein. The concentration of the galloylated and/or non-galloylated catechin in such formulations will typically be such that application in a single dosage unit will result in a local concentration of less than 1 mg/ml.

Based on these and further considerations, the inventors therefore contemplate a method of reducing MIC of an antibiotic drug in MRSA in which the *Staphylococcus aureus* is exposed to a galloylated catechin at a concentration effective to reduce the MIC of the antibiotic drug to a first level. In another step, it is recognized (e.g., via written or displayed information) that application of a non-galloylated catechin further synergistically decreases the MIC of the antibiotic drug from the first level to a second level, and in still another step, the *Staphylococcus aureus* is exposed to the non-galloylated catechin in the presence of the galloylated catechin at a concentration effective to reduce the MIC of the antibiotic drug to the second level. For example, in a typical application, suitable first levels are equal or less than 50% of the MIC of the antibiotic drug without exposing the *Staphylococcus aureus* to the galloylated catechin, and suitable second levels are equal or less than 5% of the MIC of the antibiotic drug without exposing the *Staphylococcus aureus* to the galloylated catechin. In such examples, the inventors discovered that the MRSA was exposed to the galloylated catechin at a concentration of less than 10 microgram/ml and to the non-galloylated catechin at a concentration of equal or less than 50 microgram/ml. In other examples, the inventors found that the first level was equal or less than 5% of the MIC and that the second level was equal or less than 0.5% of the MIC.

Therefore, suitable methods also include methods of suppressing growth of MRSA in which the MRSA is exposed to a combination of a galloylated catechin and an antibiotic drug, wherein the galloylated catechin and the antibiotic drug are present at a concentration (e.g., ECG at a concentration of 5 microgram/ml, and beta-lactam antibiotic at a concentration of 60 microgram/ml) ineffective to suppress growth. In another step, the MRSA is then exposed to a non-galloylated catechin (e.g., EC or EGC at a concentration of at least 25 mcg/ml, and more typically at least 50 mcg/ml) in the presence of the combination at a concentration effective to suppress growth of the MRSA. Such methods are particularly desirable to convert an MRSA (e.g., BB568, EMRSA-16, and EMRSA-15) from a resistant or intermediate character (with respect to a particular antibiotic drug) to a sensitive character.

In still further contemplated aspects, drug compositions are thus contemplated that include a galloylated catechin (e.g., ECG or EGCG), a non-galloylated catechin (EC or EGC), and optionally an antibiotic drug (e.g., a beat-lactam antibiotic), wherein the non-galloylated catechin is present at a concentration to synergistically reduce a minimum inhibitory concentration of the antibiotic drug with respect to the galloylated catechin. Such compositions are typically further associated with an information that the galloylated catechin and the non-galloylated catechin are present in a synergistic combination that reduces the MIC of the antibiotic drug with respect to the galloylated catechin. Among other suitable ratios, the non-galloylated catechin and the galloylated catechin are present in a weight ratio of at least 1:1, more typically at least 3:1, and even more typically at least 6:1. As already discussed above, it should be recognized that the composition may be formulated in numerous manners, including oral and topical formulations. However, it is particularly preferred that the formulation is a topical formulation.

EXPERIMENTS

Enhanced Binding of ECG to Membranes Mediated By EC

As *S. aureus* membranes are uniquely composed of phosphatidylglycerol (63-74%), lysylphosphatidylglycerol (17-22%), and cardiolipin (5-15%), the inventors determined the capacity of non-galloylated catechins to enhance ECG binding to *S. aureus* using the HPLC assay described by Kajiya et al (Kajiya, K., S. Kumazawa, and T. Nakayama. 2001. Steric effects on the interaction of tea catechins with lipid bilayers. *Biosci. Biotechnol. Biochem.* 65:2638-2643). EC, EGC, ECG and EGCG were provided by the Tokyo Food Techno Co. Ltd., Tokyo, Japan. *S. aureus* BB568 is a constitutive PBP2a producer (provided by B. Berger-Bächi, University of Zürich), and EMRSA-15 and EMRSA-16 were clinical isolates from the Royal Free Hospital, London. Binding of ECG to mid-logarithmic EMRSA-16 cells was enhanced by EC at concentrations of 25 mcg/ml. 13% of the EC pool bound after 20 min incubation at 35° C., and 22% of ECG was associated with the cells. In the presence of EC, ECG binding rose to 41%. EC binding was also enhanced by the presence of ECG (35.5%). EC appears, therefore, to facilitate ECG binding to staphylococcal cells as well as to PC and PE liposomes.

Sensitization Test with *S. aureus*

To investigate if this cooperative binding elicited enhanced biological activity, the capacity of EC and EGC to increase the degree of sensitization of *S. aureus* to oxacillin was determined. Checkerboard MIC assays were performed in 96-well microtiter trays with an inoculum of about $10^4$ CFU in 200 μl of Mueller-Hinton broth (Oxoid, Basingstoke, United Kingdom) supplemented with 2% NaCl. MIC values were obtained after incubation at 35° C. for 24 h. *S. aureus* ATCC29213 was used as the standard susceptible strain. Fractional inhibitory concentration (FIC) indices for triple combinations were calculated as follows: $\Sigma FIC = FIC_{OXA} + FIC_B + FIC_C = [C^{comb}_{OXA}/MIC^{OXA}] + [C^{comb}_B/MIC_B] + [C^{comb}_C/MIC_C]$, where $C^{comb}_B$, and $C^{comb}_C$ are the concentrations of catechins tested. $C^{comb}_{OXA}$ is the lowest concentration of oxacillin in the combination that inhibited growth, and $MIC_{OXA}$, $MIC_B$ and $MIC_C$ are the MICs of the compounds when used alone. For combinations of two compounds the term ($C^{comb}_C/MIC_C$) was omitted. An FIC index of $\leq 0.5$ indicates synergy.

We determined the effect of EC, EGC and EGCG on the capacity of ECG to sensitize EMRSA-16, EMRSA-15 and BB568 to oxacillin, and the results for these experiments are listed in FIG. 2A. The MICs of oxacillin for BB568, EMRSA-16 and EMRSA-15 were 256, 512 and 16 mg/ml, respectively. The catechin compounds had little or no intrinsic anti-staphylococcal activity, with MICs ranging from 64-512 mg/ml. An ECG concentration of 12.5 mg/ml reduced the oxacillin MIC for *S. aureus* BB568 and EMRSA-16 to below the oxacillin breakpoint; a similar effect was achieved for EMRSA-15 with the lower concentration of 3.12 mg/ml. Remarkably, the non-galloylated catechins EC and EGC were unable to reduce the MIC of oxacillin against these isolates. However, these compounds markedly enhanced the capacity of ECG to reduce oxacillin resistance. A concentration of 3.12 mg/ml of ECG reduced the MICs to 64 and 128 mg/ml for BB568 and EMRSA-16, respectively. In combination with 6.25 mg/ml of EC, oxacillin susceptibility increased to 8 mg/ml for these isolates; increasing the EC concentration to 25 mg/ml produced values of 2 mg/ml in the presence of 3.12 mg/ml of ECG. Similar reductions were observed when EGC was used in combination with ECG. FIC indices indicated strong synergy between oxacillin, ECG and either EC or EGC against all three *S. aureus* isolates. At high concentrations, a combination of ECG ($\geq$12.5 mg/ml) with both EC and EGC ($\geq$50 mg/ml) inhibited the growth of EMRSA-16 in the absence of oxacillin.

The enhancement by EC and EGC of ECG-mediated sensitization to oxacillin was clearly concentration dependent, as illustrated in FIG. 1 (depicting the effect of ECG and EC on oxacillin MICs for EMRSA-16). The galloylated catechin EGCG was significantly less effective at reducing the MIC for oxacillin in the presence of ECG. For example, with 3.12 mg/ml of ECG, 25 mg/ml of EGCG reduced the MIC only twofold. At the higher ECG concentration of 12.5 mg/ml, EGCG compromised the capacity of ECG to reduce the MICs for strains BB568 and EMRSA-16. EGCG was also able to sensitize BB568, EMRSA-16 and EMRSA-15 to oxacillin (see FIG. 2B) but the effect was much less pronounced than that associated with ECG. Both EC and EGC could enhance sensitization (as shown in FIG. 2B), but the affect was correspondingly less in comparison to [EC/EGC-ECG-oxacillin] combinations, as shown in FIG. 2A.

The inventors therefore contemplate that the capacity of non-galloylated catechins such as EC and EGC enhance the oxacillin susceptibility of MRSA strains by the galloyl catechins ECG and EGCG via targeting of the staphylococcal cytoplasmic membrane. Such hypothesis would be confirmed by the increased ECG membrane binding in the presence of EC or EGC if there was a causal connection between membrane binding and sensitivity. In further support of such hypothesis is the fact that catechins generally do not enter cells, which makes it more likely that they may modulate beta-lactam resistance in *S. aureus* by alteration of biophysical properties of the membrane (e.g., by compromising the function of proteins associated with the bilayer and thus affecting transport of materials across the membrane).

The above data clearly demonstrate the significant and synergistic character of the interaction between galloylated and non-galloylated catechins in the presence of an antibiotic with regard to their antimicrobial effect. Such finding is particularly surprising as previous studies have suggested that the gallate group is essential for epicatechin gallate activity (Stapleton, P. D., S. Shah, J. C. Anderson, Y. Hara, J. M. T. Hamilton-Miller, and P. W. Taylor. 2004. Modulation of beta-lactam resistance in *Staphylococcus aureus* by catechins and gallates. *International J. Antimicrol. Agents* 23:462-467). Furthermore, it is unlikely that the non-galloylated catechins act as an esterase inhibitor as these compounds lack an ester group. In addition, esterase-stable derivatives of ECG have similar activities when used in combination with oxacillin against *S. aureus*, suggesting esterase activity is not a critical factor in vitro (Anderson, J. C., C. Headley, P. D. Stapleton, and P. W. Taylor. 2005. Synthesis and antibacterial activity of a hydrolytically stable (−)-epicatechin gallate analogue for the modulation of beta-lactam resistance in *Staphylococcus aureus*. *Bioorg. Med. Chem. Lett.* 15:2633-2635). However, it is noted that other forms of inactivation, and particularly modification to the catechin moiety, where EC and EGC could act as potential inhibitors, cannot be ruled out.

Thus, specific embodiments and applications of compositions and methods of sensitizing MRSA to oxacillin have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. An antibiotic drug composition, comprising:
   a galloylated catechin, a non-galloylated catechin, and an antibiotic drug, wherein the antibiotic drug is a beta-lactam antibiotic;
   wherein the non-galloylated catechin is present at a concentration to synergistically reduce a minimum inhibitory concentration of the antibiotic drug with respect to the galloylated catechin, and wherein the non-galloylated catechin and the galloylated catechin are present in a weight ratio of at least 3:1; and
   an information associated with the composition that the galloylated catechin and the non-galloylated catechin are present in a synergistic combination that reduces the minimum inhibitory concentration of the antibiotic drug with respect to the galloylated catechin.

2. The antibiotic drug composition of claim 1 wherein the galloylated catechin is ECG or EGCG.

3. The antibiotic drug composition of claim 1 wherein the non-galloylated catechin is EC or EGC.

4. The antibiotic drug composition of claim 1 wherein the non-galloylated catechin and the galloylated catechin are present in a weight ratio of at least 6:1.

5. The antibiotic drug composition of claim 1 wherein the antibiotic drug is a beta-lactam antibiotic is selected from the group consisting of an oxacillin, methicillin, and a penicillin.

6. The antibiotic drug composition of claim 1 wherein the composition is formulated as a topical composition.

7. A method of suppressing growth of a methicillin resistant strain of *Staphylococcus aureus*, comprising:
   exposing the *Staphylococcus aureus* to a combination of a galloylated catechin and an antibiotic drug, wherein the antibiotic drug is a beta-lactam antibiotic, wherein the galloylated catechin and the antibiotic drug are present at a concentration ineffective to suppress growth; and
   exposing the *Staphylococcus aureus* to a non-galloylated catechin in the presence of the combination at a concentration effective to suppress growth of the *Staphylococcus aureus*, wherein the non-galloylated catechin and the galloylated catechin are present in a weight ratio of at least 3:1.

8. The method of claim 7 wherein the antibiotic drug is at a concentration of 60 microgram/ml, and wherein the galloylated catechin is ECG at a concentration of 5 microgram/ml.

9. The method of claim 8 wherein the non-galloylated catechin is EC or EGC at a concentration of at least 25 microgram/ml.

10. The method of claim 7 wherein the non-galloylated catechin is EC or EGC at a concentration of at least 50 microgram/ml.

11. The method of claim 7 wherein the *Staphylococcus aureus* is selected from the group consisting of BB568, EMRSA-16, and EMRSA-15.

* * * * *